United States Patent [19]

Saito et al.

[11] 4,448,733

[45] May 15, 1984

[54] PRODUCTION OF ALKYLSULFINYL SUBSTITUTED ORGANOPHOSPHORIC ACID ESTERS

[75] Inventors: Junichi Saito, Tokyo; Kozo Shiokawa, Kanagawa; Toshiyuki Takemoto, Tokyo, all of Japan

[73] Assignee: Nihon Tokushu Noyaku Seizo K.K., Tokyo, Japan

[21] Appl. No.: 366,101

[22] Filed: Apr. 6, 1982

[30] Foreign Application Priority Data

Apr. 6, 1981 [JP] Japan .................................. 56-50536

[51] Int. Cl.³ .......................... C07F 9/09; C07F 9/165
[52] U.S. Cl. .................................................. 260/985
[58] Field of Search ......................................... 260/985

[56] References Cited

U.S. PATENT DOCUMENTS

| | | |
|---|---|---|
| 2,938,919 | 5/1960 | Lorenz et al. ........................ 260/985 |
| 2,999,874 | 9/1961 | Schrader ............................. 260/985 |
| 3,042,703 | 7/1962 | Schegk et al. ....................... 260/985 |
| 3,112,269 | 11/1963 | Calhoun et al. ..................... 260/985 |

FOREIGN PATENT DOCUMENTS

| | | |
|---|---|---|
| 1101406 | 3/1961 | Fed. Rep. of Germany . |
| 2420526 | 10/1979 | France . |
| 778759 | 7/1957 | United Kingdom . |
| 819689 | 9/1959 | United Kingdom . |

OTHER PUBLICATIONS

Union Carbide, Abstract of French 2,420,526, vol. 92, (1980), 128409g.

*Primary Examiner*—Anton H. Sutto

*Attorney, Agent, or Firm*—Sprung, Horn, Kramer & Woods

[57] ABSTRACT

A process for preparing an alkylsulfinyl-substituted phenylphosphoric acid ester of the formula

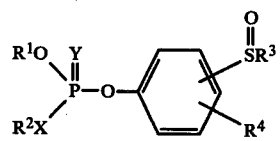

in which
  $R^1$ and $R^2$ each independently is alkyl, haloalkyl, alkenyl or optionally substituted aryl,
  $R^3$ is alkyl,
  $R^4$ is hydrogen, halogen, alkyl, alkoxy, nitro, cyano, alkoxycarbonyl group, phenyl or phenoxy, and
  X and Y each independently is oxygen or sulfur, which comprises reacting hydrogen peroxide with an alkylmercapto-substituted phenylphosphoric acid ester of the formula

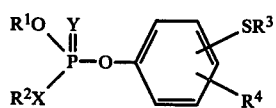

in an aprotic solvent under sulfuric acid-induced acidic conditions in the presence of an organic carboxylic acid. The product is obtained in higher purity and yield.

6 Claims, No Drawings

PRODUCTION OF ALKYLSULFINYL SUBSTITUTED ORGANOPHOSPHORIC ACID ESTERS

This invention relates to an improved process which can produce an alkylsulfinyl-substituted phenylphosphoric acid ester from an alkylmercapto-substituted phenylphosphoric acid ester with advantage on a commercial scale, at lower production costs, with safety, with markedly improved purity and in better yields while advantageously avoiding various drawbacks and troubles encountered in commercial-scale practice.

It is known to produce an alkylsulfinyl-substituted phenylphosphoric acid ester useful as an insecticidal and acaricidal compound by reacting hydrogen peroxide with an alkylmercapto-substituted phenyl-phosphoric acid ester. It was difficult, however, to produce advantageously the desired compound with high purity and in high yields by a procedure suitable for commercial practice because of various problems and drawbacks.

Japanese Patent Publication No. 778/60, for example discloses such reaction using hydrogen peroxide in acetic acid as solvent. Commercial-scale execution of this method, however, was found to incur numerous troubles in separating the desired compound from the reaction products.

According to the reference, the method on a laboratory scale involves the extraction of the desired product by shaking the reaction mixture several times with an organic solvent and water. This step is carried out by pouring the reaction mixture in a large amount of water to form a mixed system of acetic acid as solvent, a large amount of water and the resulting products, and then extracting the system with an organic solvent to separate and collect the desired product. This requires a vast amount of the organic solvent for separation and collection of the intended product, and necessitates treatment of a large amount of effluent containing acetic acid. Further, the recovery of acetic acid from the acetic acid-containing effluent is commercially very disadvantageous and difficult, and requires large facilities for the treatment of the effluent. Thus, such method poses many technical problems impeding commercial-scale practice.

Concerning this method, this publication proposed another laboratory-scale procedure in which the reaction system consisting of hydrogen peroxide and the reaction products in an acetic acid solvent was directly distilled to recover acetic acid. This procedure is difficult to perform safely and incurs the danger of explosion. This procedure, therefore, is unacceptable for commercial-scale practice.

Japanese Patent Publication No. 778/60 also discloses a method for the reaction with hydrogen peroxide in methanol as solvent under sulfuric acid-induced acidic conditions. This method was found to be defective in that when it is practiced on a commercial scale, many troubles are incurred in separating the desired object from the reaction products, and the method per se is troublesome.

The commercial-scale execution of the reaction method involves the aforementioned troubles in treating effluent containing methanol, and the recovery and recycle of methanol require complicated and disadvantageous steps and costly distillation equipment.

This publication describes the reaction temperature as 40°-50° C. Followup studies by the inventors of the present invention showed that the reaction proceeds slowly, and the complete advance of the reaction on a commercial scale requires a lengthy reaction time and a reaction temperature of 40°-50° C., and in some cases, of about 60° C. This poses the risk of causing an abnormal reaction. This method therefore was found to be unsuitable for commercial-scale practice.

The inventors of this invention have made studies to develop a process suitable for producing an alkylsulfinyl-substituted phenylphosphoric acid ester from an alkylmercapto-substituted phenylphosphoric acid ester on a commercial scale.

The conventional method comprised reacting hydrogen peroxide with an alkylmercapto-substituted phenylphosphoric acid ester in highly polar methanol under acidic conditions involving a small amount of sulfuric acid or in a highly polar acetic acid solvent to oxidatively convert the alkylmercapto group into an alkylsulfinyl group under the oxidizing force of the resulting organic peracid. The studies by the inventors led to the discovery that when this reaction is carried out in an aprotic solvent under acidic conditions involving a small amount of sulfuric acid in the presence of an organic carboxylic acid in a non-solvent amount, say, a markedly decreased amount as small as 1 mol or less per mol of the starting ester, the aforementioned drawbacks or troubles with the conventional methods can be avoided advantageously and an alkyl-sulfinyl-substituted phenylphosphoric acid ester can be prepared on a commercial scale along with various improvements such as very high purity and high yields, simplified procedures, lower costs, high safety, good qualitative reproducibility, markedly reduced amounts of organic carboxylic acids used, low reaction temperatures, shortened reaction time, and better effluent treatment.

Specifically, this invention relates to a process for preparing an alkylsulfinyl-substituted phosphoric acid ester of the formula

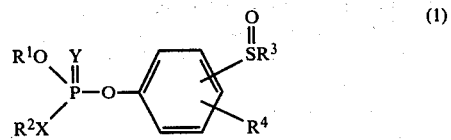 (1)

in which
R$^1$ and R$^2$ each independently is alkyl, haloalkyl, alkenyl or optionally substituted aryl,
R$^3$ is alkyl,
R$^4$ is hydrogen, halogen, alkyl, alkoxy, nitro, cyano, alkoxycarbonyl, phenyl or phenoxy, and
X and Y each independently is oxygen or sulfur, which comprises reacting hydrogen peroxide with an alkylmercapto-substituted phenylphosphoric acid ester of the formula

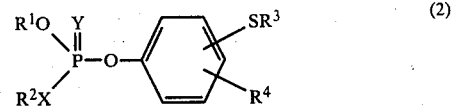 (2)

in an aprotic solvent under sulfuric acid-induced acidic conditions in the presence of an organic carboxylic acid.

Scaled-up experiments have shown that when the above reaction is performed with hydrogen peroxide in methanol as a solvent under sulfuric acid-induced acidic conditions at a reaction temperature of about room temperature or in the range of 40° to 50° C., the results obtained are unsatisfactory in purity and yield, as many Comparison Examples and Synthesis Examples hereinbelow will show. The method of the present invention, on the other hand, has been found to produce the desired product at a low reaction temperature and a shortened reaction time which are of commercial advantage.

An object of this invention is therefore to provide an improved process capable of preparing an alkylsulfinyl-substituted phenylphosphoric acid ester from an alkylmercapto-substituted phenylphosphoric acid ester commercially advantageously.

This and many other objects and advantages of this invention will become more apparent from the following description.

The reaction scheme of the novel process can be expressed as follows:

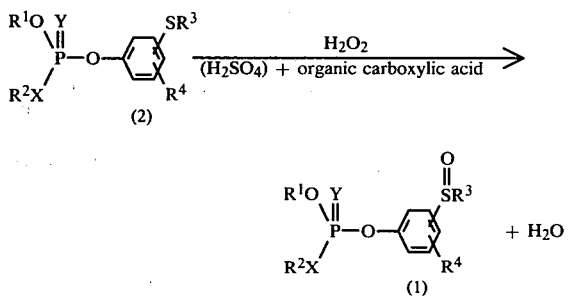

Examples of $R^1$ and $R^2$ include $C_1$–$C_8$, preferably, $C_1$–$C_6$ alkyl groups, such as methyl, ethyl, n-(or iso-)propyl, n-(iso-, sec- or tert-)butyl, n-(or iso-)amyl, or n-hexyl; halo-substitution products thereof, preferably, $C_1$–$C_6$ alkyl groups, e.g., chlorine-, bromine-, fluorine- or iodine-substituted alkyl groups; $C_2$–$C_6$, preferably $C_2$–$C_4$ alkenyl groups such as vinyl, allyl or methallyl; and $C_6$ and $C_{10}$ aryl groups, such as phenyl and naphthyl groups optionally having substituents selected from the group consisting of $C_1$–$C_4$ lower alkyl, halogen atoms, $C_1$–$C_4$ lower alkoxy, and nitro.

Examples of $R^3$ include $C_1$–$C_4$, preferably, $C_1$–$C_2$ lower alkyl groups.

Examples of $R^4$ include a hydrogen atom, a nitro group, a cyano group, a phenoxy group, and a halogen atom as exemplified with regard to the above-described haloalkyl groups; $C_1$–$C_4$, preferably, $C_1$–$C_2$ lower alkyl groups, e.g., lower alkyl groups having carbon atoms within said range among those exemplified with regard to $R^1$ and $R^2$; $C_1$–$C_4$ lower alkoxy groups such as methoxy, ethoxy, and n-(or iso-) propoxy, n-(iso-, sec- or tert-)butoxy; and lower alkoxycarbonyl groups having the same alkoxy groups as said lower alkoxy groups.

Examples of starting compounds of formula (2) are O,O-dimethyl-O-(3-methyl-4-methylthio-phenyl)thiophosphate, O,O-diethyl-O-(3-methyl-4-methylthio-phenyl) thiophosphate, O,O-dimethyl-O-(4-methylthio-phenyl)thio-phosphate, O,O-diethyl-O-(4-methylthio-phenyl)thiophosphate; and O-ethyl-S-n-propyl-O-(4-methylthiophenyl)phosphorodithioate. Examples of compounds of formula (1) include O,O-dimethyl-O-(3-methyl-4-methylsulfinylphenyl)thiophosphate, O,O-diethyl-O-(3-methyl-4-methylsulfinylphenyl)thiophosphate, O,O-dimethyl-O-(4-methylsulfinylphenyl)thiophosphate, O,O-diethyl-O-(4-methylsulfinylphenyl)thiophosphate, and O-ethyl-S-n-propyl-O-(4-methylsulfinylphenyl)phosphorodithioate.

According to the method of the present invention, the reaction of hydrogen peroxide with the above-exemplified compound of formula (2) for the preparation of the above-exemplified compound of formula (1) is carried out in an aprotic solvent under sulfuric acid-induced acidic conditions in the presence of an organic carboxylic acid.

The reaction is performed in at least one aprotic organic solvent substantially immiscible with or insoluble in water, preferably selected from the group consisting of hydrocarbons, halogenated hydrocarbons, ethers and ketones. Examples of such aprotic organic solvents are aliphatic, alicyclic and aromatic (optionally chlorinated) hydrocarbons, such as hexane, cyclohexane, petroleum ether, ligroin, benzene, toluene, xylene, methylene chloride, chloroform, carbon tetrachloride, ethylene chloride and trichloroethylene, and chlorobenzene; ethers such as diethyl ether, methyl ethyl ether, diisopropyl ether, and dibutyl ether; and ketones such as methyl isobutyl ketone. These solvents may be used alone or in admixtures.

Furthermore, the reaction is performed in the aprotic solvent under sulfuric acid-induced acidic conditions in the presence of an organic carboxylic acid.

Preferred examples of organic carboxylic acids are organic carboxylic acids selected from the group consisting of formic acid, acetic acid and propionic acid optionally substituted with halogen atoms, and chlorobenzoic acid. Examples of the halogen-substituted acids are monochloroacetic acid, dichloroacetic acid and trichloroacetic acid. The chlorobenzoic acid includes, for example, m-chlorobenzoic acid.

According to the process of this invention, the reaction of the compound of formula (2) with hydrogen peroxide is carried out in the exemplified aprotic solvent under sulfuric acid-induced acidic conditions in the presence of the exemplified organic carboxylic acid. The amount of the organic carboxylic acid used may be as considerably less than 1 mol per mol of the compound of formula (2). For instance, the organic carboxylic acid may be used in an amount of about 0.05–1 mol, preferably, about 0.1–about 0.8 mol, per mol of the compound of formula (2). The amount of sulfuric acid used may be small, for instance, its amount is about 0.01–about 0.6 mol, preferably, about 0.04–about 0.5 mol, per mol of compound of formula (2).

The reaction proceeds smoothly at room temperature. However, the reaction temperature may range, for instance, from about 0° to about 25° C., preferably, from about 0° to about 20° C. The reaction time may be selected suitably; for instance, it may be from about 2 to about 4 hours.

According to the process of this invention, after the reaction has been completed, the high-purity compound of formula (1) can be easily separated and collected from the reaction products in, say, the following manner:

Since the reaction uses an aprotic organic solvent, the reaction products separate into an organic phase containing the desired product and an aqueous phase. The aqueous phase is first removed, the remaining organic phase is treated with an alkali and washed with water, and the solvent is removed by distillation, thereby obtaining the desired product. If desired, recrystallization or distillation may be conducted to increase the purity of the final product further. The aqueous phase separated can be discharged after a simple procedure, say, treatment with hypochlorous acid, since its COD and total-P concentration are both very low as the following examples illustrate.

Synthesis Examples and Comparison Examples are given below to illustrate this invention in more detail.

SYNTHESIS EXAMPLE 1 (process of this invention)

9.7 Kilograms (35 mols) of O,O-dimethyl-O-(3-methyl-4-methylthiophenyl)phosphorothioate were dissolved in 10 liters of toluene, and 1.4 liters (30 mols) of formic acid and 1.4 liters (13 mols) of 50% $H_2SO_4$ were added stirring the mixture, 3.7 kg (38.5 mols) of 35% $H_2O_2$ were added dropwise over the course of 2 hours such that a temperature of 0°–10° C. was maintained. Immediately after dropwise addition, checks by gas chromatography showed the reaction to be 86.7% complete. The, mixture was stirred for 2 hours at the same temperature, and then the aqueous phase was separated from the reaction mixture. The remaining organic phase was neutralized with 20% NaOH, and the slight excess of $H_2O_2$ was decomposed with an aqueous solution of sodium thiosulfate, followed by separating the aqueous phase. The organic phase was washed with a 1% aqueous solution of NaOH, and then washed with water. The toluene was removed by vacuum distillation to obtain 10.1 kg of the desired product, O,O-dimethyl-O-(3-methyl-4-metylsulfinylphenyl)phosphorothioate. Gas chromatography and liquid chromatography analyses showed that this product had a purity of 95.7%, a net yield of 94.1% and a melting point of 48° to 50° C.

COMPARISON EXAMPLE 1

The method of Synthesis Example 1 was performed without the use of 50% sulfuric acid. The reaction immediately after the dropwise addition was 37.4% complete. Even after 16-hour's stirring at the same temperature, the reaction was only 51.6% complete. Then, the reaction mixture was heated for 2 hours at 40° C., and the same procedure was repeated to obtain 8.9 kg of the desired product. Analyses showed this product to have a purity of 61.3% and a net yield of 53.3%.

COMPARISON EXAMPLE 2

The method of Synthesis Example 1 was performed without the use of formic acid. The reaction immediately after the dropwise addition was 5.3% complete. After 16-hour's stirring at the same temperature, the extent of reaction rose to 21.3%. Then, the reaction mixture was heated at 40°–50° C., but the extent of reaction was still only 35.7% (yield: 8.8 kg), and most of the material other than the desired product consisted of unreacted starting material.

SYNTHESIS EXAMPLE 2 (process of this invention)

9.7 kg (35 mols) of O,O-dimethyl-O-(3-methyl-4-methylthiophenyl)phosphorothioate were dissolved in 10 liters of chloroform. To the solution were added 1.4 liters (30 mols) of formic acid and 1.4 liters of 50% $H_2SO_4$. While the mixture was being stirred, 3.7 kg (38.5 mols) of 35% $H_2O_2$ was added dropwise such that the temperature was maintained at 0°–10° C. The reaction immediately after the dropwise addition was 89.2% complete. The reaction mixture was further stirred for 1 hour at the same temperature, and treated in customary manner to obtain the desired product in a yield of 10.2 kg. This product had a purity of 92.1%. The net yield was 92.2%.

COMPARISON EXAMPLE 3 (method in accordance with the description of Japanese Patent Publication No. 778/60)

10.2 kg (35 mols of O,O-diethyl-O-(4-methylthiophenyl)phosphorothioate were dissolved in 28 liters of acetic acid, and 3.7 kg (38.5 mols) of $H_2O_2$ were added dropwise over 2 hours at 0°–10° C. The reaction extent immediately after the dropwise addition was 66.5%. After 16-hour's stirring at the same temperature, the extent of reaction was 82.4%. In order to isolate the desired product from the reaction mixture, 10 liters of toluene and about 80 liters of water were added, and the mixture was stirred thoroughly. Then, the toluene phase was separated. It was washed with a dilute aqueous solution of an alkali, and the toluene was distilled off under reduced pressure, to obtain 8.8 kg of the desired product. The purity was 81.6%, and the net yield 69.8%.

COMPARISON EXAMPLE 4 (method according to the description of Japanese Patent Publication No. 778/60)

9.7 kg (35 mols) of O,O-dimethyl-O-(3-methyl-4-methylthiophenyl)-phosphorothioate were dissolved in 20 liters of methanol. To this solution was added 0.15 liters of 50% $H_2SO_4$, and 3.7 kg (38.5 mols) of 35% $H_2O_2$ was further added dropwise over 2 hours at room temperature. The extent of reaction immediately after the dropwise addition was 63.4%. After the reaction mixture was stirred for 8 hours at the same temperature, the extent of reaction was raised to 86.6%. Stirring was continued further for 1 hour at 40°–50° C. to complete the reaction. After the reaction mixture was cooled to room temperature, 10 liters of chloroform and about 60 liters of water were added, and the mixture was stirred. The respective liquid phases were separated and treated by customary methods to obtain 9.0 kg of the desired product. The purity was 85.7% and the net yield 74.6%.

Similar methods were performed in various other Synthesis Examples and Comparison Examples. The results are shown in Table 1.

TABLE 1

| | Reactant | Product | Reaction solvent and acid added, liters |
|---|---|---|---|
| Synthesis Example 1 | 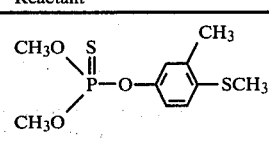 (I) 9.7 kg (35 Mols) | 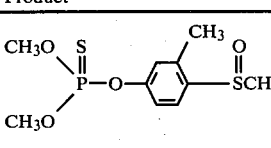 (I, S=O) 10.1 kg | Toluene 10 liters Formic acid 1.4 liters 50% Sulfuric acid 1.4 liters |

TABLE 1-continued

| | | | |
|---|---|---|---|
| Comparison Example 1 (control) | (I) 9.7 kg (35 mols) | (I, S=O) 8.9 kg | Toluene 10 liters<br>Formic acid 1.4 liters |
| Comparison Example 2 (control) | (I) 9.7 kg (35 mols) | (I, S=O) 8.8 kg | Toluene 10 liters<br>50% sulfuric acid 1.4 liters |
| Synthesis Example 2 | (I) 9.7 kg (35 mols) | (I, S=O) 10.2 kg | Chloroform 10 liters<br>Formic acid 1.4 liters<br>50% Sulfuric acid 1.4 liters |
| Comparison Example 3 (control*) | 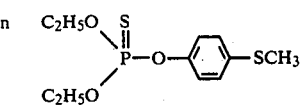<br>(II) 10.2 kg (35 mols) | 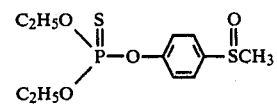<br>(II, S=O) 9.2 kg | Acetic acid 28 liters |
| Comparison Example 4 (control**) | (I) 9.7 kg (35 mols) | (I, S=O) 9.0 kg | Methanol 20 liters<br>50% Sulfuric acid 0.15 liters |
| Synthesis Example 3 | (I) 9.7 kg (35 mols) | (I, S=O) 10.1 kg | Toluene 15 liters<br>Acetic acid 1.4 liters<br>50% Sulfuric acid 1.4 liters |
| Synthesis Example 4 | (II) 10.2 kg (35 mols) | (II, S=O) 10.6 kg | Toluene 10 liters<br>Formic acid 1.4 liters<br>50% Sulfuric acid 1.4 liters |
| Synthesis Example 5 | 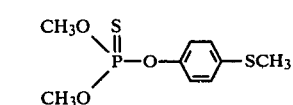<br>(III) 9.2 kg (35 mols) | 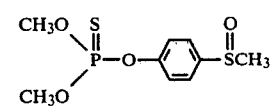<br>(III, S=O) 9.7 kg | Methyl isobutyl ketone 10 liters<br>Formic acid 1.4 liters<br>50% Sulfuric acid 1.4 liters |
| Comparison Example 5 (control) | (III) 9.2 kg (35 mols) | (III S=O) 9.0 kg | Methanol 15 liters<br>50% Sulfuric acid 0.15 liters |
| Comparison Example 6 (control) | (III) 9.2 kg (35 mols) | (III, S=O) 8.8 kg | Methanol 15 liters<br>50% Sulfuric acid 0.15 liters |
| Comparison Example 7 (control) | (III) 9.2 kg (35 mols) | (III, S=O) 8.2 kg | Methanol 15 liters<br>50% Sulfuric acid 0.15 liters |
| Synthesis Example 6 | 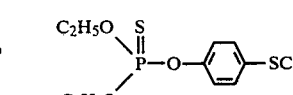<br>(IV) 11.3 kg (35 mols) | 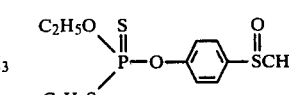<br>(IV, S=O) 11.7 kg | Toluene 12 liters<br>Formic acid 0.7 liters<br>50% Sulfuric acid 0.7 liters |
| Synthesis Example 7 | (I) 9.7 kg (35 mols) | (I, S=O) 10.2 kg | Toluene 10 liters<br>Propionic acid 1.4 liters<br>50% Sulfuric acid 1.4 liters |
| Synthesis Example 8 | (I) 9.7 kg (35 mols) | (I, S=O) 10.1 kg | Toluene 10 liters<br>Formic acid 0.35 liters<br>50% Sulfuric acid 0.5 liters |
| Synthesis Example 9 | (I) 9.7 kg (35 mols) | (I, S=O) 10.3 kg | Methyl isobutyl ketone 10 liters<br>Acetic acid 0.21 liters<br>50% Sulfuric acid 1.75 liters |
| Synthesis Example 10 | (I) 9.7 kg (35 mols) | (I, S=O) 10.1 kg | Chloroform 10 liters<br>Trichloroacetic acid 0.82 kg<br>50% Sulfuric acid 0.5 liters |

TABLE 1-continued

| Synthesis Example 11 | (V) 10.7 kg (35 mols) | (V, S=O) 11.2 kg | Toluene 10 liters<br>Formic acid 0.92 liters<br>50% Sulfuric acid 0.92 liters |

Structures: Synthesis Example 11 shows $(C_2H_5O)_2P(=S)-O-C_6H_3(CH_3)-SCH_3$ (V) converted to $(C_2H_5O)_2P(=S)-O-C_6H_3(CH_3)-S(=O)CH_3$ (V, S=O).

| | H$_2$O$_2$ | Reaction temperature and reaction time | Yield (%) | Purity (%) | Net Yield (%) | Properties and others |
|---|---|---|---|---|---|---|
| Synthesis Example 1 | 3.7 kg (38.5 mols) | 0–10° C. 4 hrs | 98.3 | 95.7 | 94.1 | m.p. 48–50° C. |
| Comparison Example 1 (control) | 3.7 kg | 10–20° C., 16 hrs, and then 40° C., 2 hrs. | 87.0 | 61.3 | 53.3 | Recovery of starting material: 36% |
| Comparison Example 2 (control) | 3.7 kg | 10–20° C., 16 hrs, and then 40° C., 2 hrs. | 85.0 | 35.6 | 30.3 | Recovery of starting material: 60% |
| Synthesis Example 2 | 3.7 kg | 0–10° C. 3 hrs. | 99.0 | 93.1 | 92.2 | |
| Comparison Example 3 (control*) | 3.7 kg | 0–10° C. 16 hrs. | 85.5 | 81.6 | 69.8 | |
| Comparison Example 4 (control**) | 3.7 kg | Room temp. 10 hrs, and then 40–50° C., 1 hr | 87.0 | 85.7 | 74.6 | |
| Synthesis Example 3 | 3.7 kg | 10–20° C. 4 hrs | 97.8 | 93.7 | 91.6 | |
| Synthesis Example 4 | 3.7 kg | 0–10° C. 3 hrs. | 98.5 | 93.8 | 92.4 | b.p. 140–141° C./0.01 mmHg |
| Synthesis Example 5 | 3.7 kg | 0–10° C. 3 hrs | 98.8 | 94.1 | 93.0 | $n_D^{20}$ 1.5648 |
| Comparison Example 5 (control) | 3.7 kg | Room temp. 3 hrs | 91.8 | 56.2 | 51.6 | Recovery of starting material: 48% |
| Comparison Example 6 (control) | 3.7 kg | Room temp. 24 hrs. | 90.2 | 72.4 | 65.3 | |
| Comparison Example 7 (control) | 3.7 kg | 40–50° C. 5 hrs | 83.6 | 78.0 | 65.2 | |
| Synthesis Example 6 | 3.7 kg | 10–20° C. 4 hrs. | 98.8 | 94.3 | 93.2 | $n_D^{20}$ 1.5820 |
| Synthesis Example 7 | 3.7 kg | 5–10° C. 3 hrs | 99.1 | 92.8 | 92.0 | |
| Synthesis Example 8 | 3.7 kg | 10–20° C. 4 hrs | 98.5 | 93.2 | 91.8 | |
| Synthesis Example 9 | 3.7 kg | 10–20° C. 4 hrs | 100 | 92.1 | 92.1 | |
| Synthesis Example 10 | 3.7 kg | 5–10° C. 4 hrs. | 98.5 | 94.1 | 92.7 | |
| Synthesis Example 11 | 3.7 kg | 5–10° C. 4 hrs | 99.0 | 94.5 | 93.6 | $n_D^{20}$ 1.5467 |

Note:
Comparison Example 3 (control*) and Comparison Example 4 (control**) show the results obtained by the method described in Japanese Patent Publication No. 778/60 on a larger scale.

Then, influences on effluent were investigated, and the following results obtained. CODs were determined in accordance with the JIS Standard K-0102.

TABLE 2

| | Amount of effluent liters | COD Mn (ppm) | COD load (g)/kg of product | total-P concentration (ppm) |
|---|---|---|---|---|
| Synthesis Example 1 | 43 | 1,700 | 7.5 | 230 |
| Synthesis Example 2 | 43 | 1,620 | 7 | 245 |
| Synthesis Example 3 | 42 | 1,520 | 7 | 264 |
| Comparison Example 3 (control*) | 120 | 10,000 | 150 | 1,500 |
| Comparison Example 4 (control**) | 100 | 100,000 | 1,300 | 2,640 |
| Comparison Example 6 (control) | 95 | 78,950 | 750 | 3,700 |

The above table also shows that the COD values and total-P concentrations in accordance with the novel process are both very low, and the influences on the environment can be minimized by simple effluent-treating methods.

It will be appreciated that the instant specification and examples are set forth by way of illustration and not limitation, and that various modifications and changes may be made without departing from the spirit and scope of the present invention.

We claim:

1. A process for preparing an alkylsulfinyl-substituted phenylphosphoric acid ester of the formula

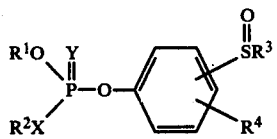

in which
R$^1$ and R$^2$ each independently is alkyl, haloalkyl, alkenyl or optionally substituted aryl,
R$^3$ is alkyl,
R$^4$ is hydrogen, halogen, alkyl, alkoxy, nitro, cyano, alkoxycarbonyl group, phenyl or phenoxy, and
X and Y each independently is oxygen or sulfur,
which comprises reacting hydrogen peroxide with an alkylmercapto-substituted phenylphosphoric acid ester of the formula

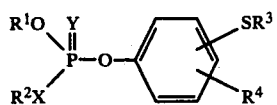

in an aprotic solvent under sulfuric acid-induced acidic conditions in the presence of an organic carboxylic acid.

2. A process according to claim 1, wherein the organic carboxylic acid is an organic carboxylic acid selected from the group consisting of formic acid, acetic acid, propionic acid, and halogen substitution products thereof.

3. A process according to claim 1, wherein the organic carboxylic acid is present in about 0.1 to 8.0 mol per mol of alkylmercapto-substituted phenylphosphoric acid ester.

4. A process according to claim 1, wherein the aprotic solvent is at least one of a hydrocarbon, halogenated hydrocarbon, ether and ketone.

5. A process according to claim 1, in which
R$^1$ and R$^2$ each independently is C$_{1-8}$-alkyl, C$_{1-6}$-haloalkyl, C$_{2-4}$-alkenyl, or phenyl or naphthyl optionally substituted by C$_{1-4}$-alkyl, halogen, C$_{1-4}$-alkoxy or nitro,
R$^3$ is C$_{1-4}$-alkyl, and
R$^4$ is hydrogen, halogen, C$_{1-4}$-alkyl, C$_{1-4}$-alkoxy, nitro, cyano, C$_{1-4}$-alkoxycarbonyl or phenoxy.

6. A process according to claim 5, wherein the organic carboxylic acid is an organic carboxylic acid selected from the group consisting of formic acid, acetic acid, propionic acid, and halogen substitution products thereof and is present in about 0.1 to 0.8 mol per mol of alkylmercapto-substituted phenylphosphoric acid ester, and the aprotic solvent is at least one of a hydrocarbon, halogenated hydrocarbon, ether and ketone.

* * * * *